(12) United States Patent
Tang et al.

(10) Patent No.: US 8,628,806 B2
(45) Date of Patent: Jan. 14, 2014

(54) HYPOLIPIDEMIC COMPOSITION AND ITS USE

(75) Inventors: Like Tang, Hangzhou (CN); Dianwu Guo, Hangzhou (CN); Chunxia Wu, Hangzhou (CN); Kai Tang, Hangzhou (CN); Tianjia Xu, Hangzhou (CN)

(73) Assignee: Hangzhou Minsheng Pharmaceutical Co., Ltd., Hangzhou, Zhejiang Province (CN)

( * ) Notice: Subject to any disclaimer, the term of this patent is extended or adjusted under 35 U.S.C. 154(b) by 634 days.

(21) Appl. No.: 12/441,899

(22) PCT Filed: Sep. 26, 2007

(86) PCT No.: PCT/CN2007/070785
§ 371 (c)(1), (2), (4) Date: Aug. 25, 2009

(87) PCT Pub. No.: WO2008/037222
PCT Pub. Date: Apr. 3, 2008

(65) Prior Publication Data
US 2010/0021575 A1    Jan. 28, 2010

(30) Foreign Application Priority Data
Sep. 27, 2006   (CN) .......................... 2006 1 0053639

(51) Int. Cl.
*A61K 36/00*    (2006.01)

(52) U.S. Cl.
USPC ........................................ 424/725; 424/773

(58) Field of Classification Search
None
See application file for complete search history.

(56) References Cited

U.S. PATENT DOCUMENTS 6,039,954 A * 3/2000 Yu et al. ........................ 424/740
2004/0071796 A1 * 4/2004 Li ................................. 424/735

FOREIGN PATENT DOCUMENTS

KR    10-2006-0023884 A    *    3/2006
KR    10-2006-0083960 A    *    7/2006

OTHER PUBLICATIONS

"Basic Tools of Herbalism" website (http://web.archive.org/web/20041211085720/http://earthnotes.tripod.com/basics.htm—internet archived version from Dec. 11, 2004).*
English translation of CN 1689629 A (2005).*

* cited by examiner

*Primary Examiner* — Susan Hoffman
(74) *Attorney, Agent, or Firm* — Yuan Qing Jiang (57) ABSTRACT

The present invention provides a hypolipidemic composition comprising peony extract and *Codonopsis* extract, or comprising water coextract of peony and *Codonopsis*, the weight ratio of the peony extract to *Codonopsis* extract in the composition is between 0.5 and 19:1. The advantages of the hypolipidemic composition are: substantially decreasing triglyceride and cholesterol, while increasing high density lipoprotein. It suggested of a favourable prospect of application.

11 Claims, 2 Drawing Sheets

HYPOLIPIDEMIC COMPOSITION AND ITS USE

FIELD OF THE INVENTION

The invention relates to a hypolipidemic composition; it further relates to a use of said composition.

BACKGROUND OF THE INVENTION

Medical research has shown that cardiovascular diseases are closely linked to the metabolism of lipids, and hyperlipemia is one of the major reasons of arteriosclerosis, particularly the increase in total cholesterol of serum indicates atherosclerosis at risk. Blood lipids, being a general term of various lipids in the serum, mainly includes: cholesterol, triglyceride, and phospholipids, and the like, together with small amount of free fatty acids (FFA) and minute quantity of other substances, such as lipsoluble vitamins, steroid hormones, and the like. Two-third of the cholesterol exist as cholesterol esters, the other one-third present themselves as free cholesterol.

At present, the number of hyperlipemia population is growing due to the substantial change of people's diet resulting from the rapidly economic development, as well as the change of factors of social psychology resulting from the rapid rhythm of lifestyle. The markedly major hypolipidemic medicines include statins (Lovastatin, Simvastatin, Pravachol and Fluvastatin) for lowering cholesterol and triglyceride; cholesterol absorption inhibitors (Cholestyramine and Colestipol); fibrates and niacins, and the like. Though the above medicines possess hypolipidemic effects, they have serious side effects as well. Therefore, there exists a need for hypolipidemic medicines with high effects and low side effects from Chinese traditional medicines, which are in great significance to the society.

The medicinal plant: peony (*Paeoniae Radix*), belonging to the plant in Ranunculus family, is generally selected from *Paeonia lactiflora* Pall., *Paeonia veitchii* Lynch., *Paeonia obovata* Maxim., *Paeonia mairei* Levl., *Paeonia anomala* L., with dry roots thereof being used. Their names are red peony (*Paeoniae Radix Rubra*), white peony (*Paeoniae Radix Alba*) respectively, charaterized by bitter in flavor, slight cold in nature, and entry into the liver channel. They can cool the blood, dissipate stasis and alleviate pain. It can be applied to the subjects suffering from warm toxin macular eruption, blood ejection and spontaneous external bleeding, sore red swollen eyes, liver depression rid-side pain, amenorrhvea and dysmenorrheal, abdominal mass and bellyache, knocks and falls, swelling and toxin of welling abscess and flat. Li jiakang and Jiao yang ("The effect of the radix paeoniae rubra injection on the level of blood fat in patients suffering from stoke after acupoint injected", *Chinese Acupuncture* 9:429-430 (1999)) describes a radix paeoniae rubra injection, when acupoint injected can modulate the level of blood fat. However, its pharmacological mechanism remains unknown and there is a need for further research.

*Codonopsis* (*Cidibiosutus Radix*) belongs to the dry root of Platycodon family plant: *Codonopsis pilosula* (*Franch.*) Nannf., *Codonopsis Pilosula* Nannf. var. *modesta*(Nannf.)L. T Shen, or *Codonopsis tangshen* Oliv., charaterized by sweet in flavor, neutral in nature and entry into the spleen and liver channel. It can supplement the centre and boost qi, fortify the spleen and boost lung, and could be applied to the subjects suffering from spllen-lung vacuity, shortness of breath and palpitation, poor appetite and loose stool, asthenia-type dyspnea and cough, internal heat-syndrome and diabetes. It is reported that *Codonopsis* has hypolipidemic effect. (Shen dexin and Miao kecan, "the effectiveness observed of zhuwan in treatment of hyperlipemia", *LiaoNing Chinese Medicine Journal*, 1:6-7(1980)).

Patent CN99102902.X, with title of invention "Healthy beverage for prevention and treatment of hypertension and hyperlipemia" describes healthy beverage for prevention and treatment of hypertension and hyperlipemia, which comprises extracts from *Codonopsis*, tangkuei (*Angelicae Sinensis Radix*), radix rehmanniae (*Rehmanniae Radix Exsiccata seu Recens*), ligusticum (*Ligustici Rhizoma*), red peony (*Paeoniae Radix Rubra*) and the like, totally 15 kinds of traditional Chinese medicines. Since these material is a combination of multiple Chinese medicines, it is difficult to sufficiently demonstrate the hypolipidemic effect of *Codonopsis* and peony. Currently, no report describes the composition comprising the mixture of *Codonopsis* and peony as main component having hypolipidemic activity.

CONTENT OF THE INVENTION

One object of the present invention is to provide a highly effective hypolipidemic composition.

Another object of the present invention is to provide the use of said hypolipidemic composition described herein in the preparation of medicines or health care products.

The objects of the present invention is achieve by providing a hypolipidemic composition comprising the extract from peony and extract from Codonopsis, with the weight ratio of between about 0.5 and 19:1 (0.5-19:1).

The medicinal plant peony, belonging to Ranunculus family, is generally selected from *Paeonia lactiflora* Pall., *Paeonia veitchii* Lynch., *Paeonia obovata* Maxim., *Paeonia mairei* Levl., *Paeonia anomala* L., their dry roots are commonly used.

Alternatively, the present invention generally uses Chinese medicine resource selected from red peony and white peony to obtain peony extract.

*Codonopsis* used in the present invention is the dry root of Platycodon family plant: *Codonopsis pilosula*(*Franch.*) Nannf., *Codonopsis Pilosula* Nannf. var. *modesta*(Nannf.)L. T Shen, or *Codonopsis tangshen* Oliv., which belongs to Campanulaceae.

Said peony extract is extracted with water or $C_1$~$C_8$ alcohol-water mixture. Said *Codonopsis* extract is extracted with water or $C_1$~$C_8$ alcohol-water mixture. Said alcohol-water mixture is obtained by mixing the alcohol and water in any ratio. In a preferred embodiment, percentage by volumn of the alcohol in the mixture is 50-95%. More prefably, said $C_1$~$C_8$ alcohol is ethanol or methanol.

More specifically, said peony extract is obtained by the following steps: said plant root or the powder of the plant root is extracted 1-3 times with, based on the weight of the raw material, 4~10 folds by weight of 50~95 volume% $C_1$~$C_8$ alcohol-water mixture under refluxing. The filtrate is combined, the alcohol is recovered, and the mixture is dissolved into, based on the weight of the raw material, 3~6 folds by weight of water, and filtered. The filtrates are charged into macroporous adsorbing resin, the resin is eluted with 5~70% ethanol, the eluent is concentrated and dried to obtain the said peony extract.

Said *Codonopsis* extract is made by the following steps: *Codonopsis* is extracted with, based on the weight of raw material, 4~10 folds by weight of 50~95 volume % $C_1$~$C_8$ alcohol-water mixture 1-3 times under refluxing. The filtrates are discarded. The filtrated residue is extracted with, based on the total weights of raw material, 1~3 folds by weight of water 3-6 times under refluxing. The water extracted products are combined, concentrated under reduced pressure, decolored with carbon, and then filtered. Ethanol is added into the filter cake, which is allowed to stand overnight. Filter again, the filter cake is washed with ethyl ether and absolute ethanol successively, dried to obtain said *Codonopsis pilosula* extract.

In the preferred embodiment, said hypolipidemic composition comprises peony extract and *Codonopsis* extract, in which the weight ratio of said peony extract to said *Codonopsis* extract is between 1 and 6:1 (1-6:1). More preferably, the ratio is between 2 and 3.7:1(2-3.7:1).

Specifically, said hypolipidemic composition is the mixture of peony extract and *Codonopsis* extract, in which the weight ratio of peony extract and *Codonopsis* extract is between 1 and 6:1 (1-6:1). Said peony extract is prepared by the following steps: The dry root of peony plant is ground into powders, the powders are allowed to pass through 40-mesh screen, and are extracted with, based on the total weights of raw material, 8 folds by weight of 70% ethanol twice under refluxing, each time for 2 hours. The filtrates are combined and dissolved into 4 folds by weight, based on the weight of the raw material, of hot water. Filter again, and the filtrates are charged to D101 macroporous adsorbing resin, eluted with deionized water to nearly colorless, eluted again with 20% ethanol. The eluate is collected until no color is observed, concentrated and dried to obtain the said *Paeonia* extract. Preferably, it has the following properties:

| Item | Property |
|---|---|
| Appearance | Dark yellow or brown powder |
| Smell | a little aromatic |
| Taste | bitter in taste |
| Paeoniflorin % ≥ | 10.0 |
| Mesh | 95% passed through 80-mesh |
| Loss on dry % ≤ | 5.0 |
| Heavy metals ppm ≤ | 20 |
| Arsenic salt ppm ≤ | 2 |
| Ash % ≤ | 3 |
| divinyl-benzene μg/kg ≤ | 50 |
| Total number of bacterial colony | 1000 |
| Coliform group MPN/100 g ≤ | 40 |
| Mould cfu/g ≤ | 25 |
| Yeast cfu/g ≤ | 25 |
| Pathogen (incl. *Salmonella*, *Staphylococcus Aureus*, *Shigella*, *Streptococcus hemolyticus*) | none |

Measure Methods of Contents:
1. Paeoniflorin Content:

[Content Determination] The assay is performed in accordance with the high performance liquid chromatography method (Chinese pharmacopoeia, 2005 version, Part I, Appendix VI D).
Chromatographic Condition and System Suitability Assay Octadecylsilane chemically bonded silica is used as filler; methanol-water-glacial acetic acid (27:72:1) as mobile phase; detection wave length is 232 nm; column temperature is 30° C., theoretical plate calculated based on the peak of paeoniflorin is no less than 2500. The resolution between paeoniflorin peak and adjacent peaks should comply with requirements.
Determination 10 tablets of sample are taken and the film coatings are removed. Grind them into fine powder, and then transfer accurately measured of 20.00 mg fine powder into 25 ml volumetric flask. Appropriate quantity of absolute methanol is added and dissolve is achieved by ultrasound for 20 min. The solution is allowed to stand until room temperature, and then is diluted to the destination volume with absolute methanol, shake, filter to obtain test sample solution. Transfer accurately measured 10 μl into liquid chromatograph and record chromatogram. Additional Paeoniflorin control substance is taken and accurately measured. Absolute methanol is added to form solution which comprises 0.10 mg Paeoniflorin per 1 ml solution, shaked until even, and determined as above. The content of Paeoniflorin is calculated based on peak area according to external standard method.
2. Determination of Divinyl-Benzene Transfer accurately measured of 0.3 g sample into head-space bottle, dissolve with 5 ml water, which is used as test sample solution. Additional amount of accurately measured divinyl-benzene is taken and dissolved with dimethyl formamide, then a appropriate amount is accurately taken and diluted with water to form solution which comprises 0.003 μg per 1 ml solution. Transfer an accurately measured amount into 5 ml head-space bottle, which is used as control solution. In accordance with residual solvent measurement (Chinese pharmacopoeia, Part II, Appendix VIII P, Method 2), 5% phenyl-95% Methylpolysiloxane is used as immobile liquid, temperature programming process is applied to column temperature, 70° C. is maintained for 5 min, then the temperature is raised to 170° C. with a rate of 20° C. per minute, the chromatographic peak is recorded. For the sample solution, there should be no peak of divinyl-benzene or the peak area should be less than that of corresponding peak of control solution (limit amount: 0.05 ppm).

Said *Codonopsis* extract is obtained by the following steps: Raw powders of *Codonopsis* are extracted twice with, based on the total weights of raw material, 2.5 folds by weights of petroleum ether under refluxing, each time for 30 minutes. The mixture is filtered and the filtrates are discarded. The filter residue is collected and extracted twice with, based on the weight of residue, 2.5 folds by weight of absolute ethyl ether under refluxing (based on the residue), each time for 30 minutes. The mixture is filtered and the filtrates are discarded. The filter residue is collected and extracted with, based on the weight of the residue, 5 folds by weight of 80% ethanol twice under refluxing, each time for 45 minutes. The mixture is filtered and the filtrates are discarded. The filter residue is extracted twice with, based on the weight of residue, 5 folds by weight of water under refluxing, each time for 45 minutes. The water extraction is combined, concentrated under reduced pressure to ¼ of the original volume, decolored with 0.1% active carbon for 15 minutes, and then filtered. Add ethanol into the filtrate so that the alcohol content reaches 80%, the solution is allowed to stand overnight, and then filtered. The filter cake is washed 3 times with absolute ethyl ether, and washed additional 3 times with absolute ethanol. The filter cake is dried in vacuo at 40° C. to obtain the said *Codonopsis* extract, which has the following properties:

| Item | Property |
|---|---|
| Appearance | White or light yellow powder |
| Smell | None |
| Taste | Sweet |
| Coarse polysaccharide % ≥ | 15 |
| Mesh | 95% passed through 80-mesh |
| Loss on dry % ≤ | 5.0 |
| Heavy metals ppm ≤ | 20 |
| Arsenic salt ppm ≤ | 2 |
| Ash % ≤ | 3 |

-continued

| Item | Property |
|---|---|
| Total number of bacterial colony | 1000 |
| Coliform group MPN/100 g ≤ | 40 |
| Mould cfu/g ≤ | 25 |
| Yeast cfu/g ≤ | 25 |
| Pathogen (incl. *Salmonella*, *Staphylococcus Aureus*, *Shigella*, *Streptococcus Hemolyticus*) | none |

The detection method of Coarse polysaccharide is referenced by "Detection method for the effective ingredient of health food" (edited by Wang Guangya).

The composition described in the present invention comprises peony extract and Codonopsis extract as effective ingredients. It can optionally contain small amounts of other traditional Chinese medicine ingredients to enhance the effectiveness, or pharmaceutically accepted excipients to formulate them into various dosage forms. The key point of the present invention is that the effectiveness of the medicine is maximized by controlling the weight ratio of the peony extract to *Codonopsis* extract in the composition. Experiments show that when the weight ratio is within the described range, especially between 2 and 3.7:1(2-3.7:1), the effectiveness on reducing blood lipid obtained by the hypolipidemic composition is the best.

In a further aspect, the present invention describes the use of the said hypolipidemic composition in the production of hypolipidemic health care products.

In another further aspect, the present invention describes the use of the said hypolipidemic composition in the production of hypolipidemic medicines.

The present invention also describes a lipid lowering method, which comprises administrating said hypolipidemic composition to individuals in need thereof.

The hypolipidemic effectiveness specifically includes lowering the total serum cholesterol in the individuals, lowering the serum triglyceride in the individuals and/or lowering the serum high density lipoprotein cholesterol in the individuals.

The effectiveness of the said hypolipidemic composition described by the present invention is indicated by the fact that the said hypolipidemic composition can significantly lower the triglyceride and cholesterol, and increase the high density lipoprotein, and therefore has great prospects.

MODE OF CARRYING OUT THE INVENTION

The present invention will be further illustrated in combination with the following specific examples. It should be understood that, these examples are exemplary only, not intended to limit the protection scope of the present invention.

Example 1

Preparation of Peony Extract 1 part by weight of the root of *Paeonia veitchii Lynch* was ground into powder (passed through 40-mesh screen) and extracted twice with 8 parts by weight of 70% ethanol under refluxing, each time for 2 hours. The filtrates were combined and ethanol was recovered until the absence of the alcoholic smell. The mixture was dissolved into, based on the total weights of raw material, 4 folds by weight of hot water and filtered, the filtrates were collected and charged into previously prepared D101 macroporous adsorbing resin, eluted with deionized water till nearly colorless, and then eluted with 20% ethanol. The eluate was collected until no color was observed. The eluate was concentrated and dried to obtain peony extract, in which the total content of Paeoniflorin (glucosides of red peony) was around 40% by weight.

Example 2

Preparation of Peony Extract 1 part by weight of the root of *Paeonia veitchii Lynch* was ground into powder (passed through 40-mesh screen) and extracted with 8 parts by weight of 95% ethanol twice under refluxing, each time for 2 hours. The filtrates were combined and ethanol was recovered until the absence of the alcoholic smell. The mixture was dissolved into, based on the total weights of raw material, 4 folds by weight of hot water and filtered, the filtrates were collected and charged into previously prepared AB208 macroporous adsorbing resin, eluted with deionized water till nearly colorless, and then eluted with 5% ethanol. The eluate was collected until no color was observed. The eluate was concentrated and dried to obtain peony extract, in which the total content Paeoniflorin (glucosides of red peony) was about 70% by weight.

Example 3

Preparation of Peony Extract 1 part by weight of the root of *Paeonia veitchii Lynch* was ground into powder (passed through 40-mesh screen) and extracted twice with 8 parts by weight of 70% ethanol under refluxing, each time for 2 hours. The filtrates were combined and ethanol was recovered until the absence of the alcoholic smell. The mixture was dissolved into, based on the total weights of raw material, 4 folds by weight of hot water and filtered, the filtrates were collected and charged into previously prepared AB101 macroporous adsorbing resin, eluted with deionized water till nearly colorless, and then eluted with 70% ethanol. The eluate was collected until no color was observed. The eluate was concentrated and dried to obtain *Paeonia* extract, in which the total content of Paeoniflorin (glucosides of red peony) was around 50% by weight.

Example 4

Preparation of Peony Extract 1 part by weight of Traditional Chinese Medicine material—white peony powder was extracted twice with 8 parts by weight of methanol under refluxing, each time for 2 hours. The filtrates were combined and methanol was recovered until the absence of the alcoholic smell. The extract concrete was dissolved into water, extracted 3 times with equal volume of saturated n-butyl alcohol aqueous solution. The n-butyl alcohol layer was collected, n-butyl alcohol was distilled out and dried to obtain peony extract, in which the total content of Paeoniflorin was around 90% by weight.

Example 5

Preparation of Peony Extract 1 part by weight of Traditional Chinese Medicine material—red peony powder was extracted twice with 6 parts by weight of n-heptyl alcohol under refluxing, each time for 2 hours. The filtrates were combined and n-heptyl alcohol was recovered until the absence of the alcoholic smell. The extract concrete was dissolved into water, extracted 3 times with equal volume of saturated n-butyl alcohol aqueous solution. The n-butyl alcohol layer was collected, n-butyl alcohol was distilled out and dried to obtain *Paeonia* extract, in which the total content of Paeoniflorin was around 50% by weight.

Example 6

Preparation of *Codonopsis* Extract 1 part by weight of raw powder of *Codonopsis* was decocted twice with 4 parts by weight of water, each time for 1.5 hours. The extracts were combined and concentrated, the extract concrete was added certain amount of excipients, dried in vacuo to obtain *Codonopsis* extract.

Example 7

Preparation of *Codonopsis* Extract 1 part by weight of raw powder of *Codonopsis* was extracted twice with 2.5 parts by weight of petroleum ether under refluxing, each time for 30 minutes. The mixture was filtered and the filtrate was discarded. The filter residue was collected and treated with ethyl ether according to the abovementioned method. The filter residue was extracted twice with, based on the total weights of raw material, 5 folds by weight of 80% ethanol under refluxing, each time for 45 minutes. The mixture was filtered and the filtrate was discarded. The filter residue was extracted twice with, based on the total weights of raw material, 5 parts by weight of water under refluxing, each time for 45 minutes, and filter. The water extracts were combined and concentrated under reduced pressure to ¼ of the total initial volume, which was decolored with 0.1% active carbon for 15 min, and filtered. The filtrate was added ethanol so that the alcohol content therein reached 80%. The mixture was allowed to stand overnight, and filter. The filter cake was washed 3 times with ethyl ether, and then washed 3 times with absolute ethanol. The filter cake was dried in vacuum oven at 60° C. to obtain *Codonopsis* extract, in which the content of *Codonopsis* extract was about 90% by weight.

Example 8

Preparation of *Codonopsis* Extract 1 part by weight of raw powder of *Codonopsis* was extracted twice with 5 parts by weight of 70% ethanol under refluxing, each time for 45 minutes. The mixture was filtered and the filtrate was collected. The filtrate was charged into previously prepared D101 macroporous adsorbing resin, eluted with deionized water. The eluate was collected and concentrated, dried in vacuum oven at 60° C. to obtain *Codonopsis* extract, in which the content of *Codonopsis* extract was around 60% by weight.

Example 9

Preparation of *Codonopsis* Extract 1 part by weight of raw powder of *Codonopsis* was extracted twice with, based on the total weights of raw material, 5 parts by weight of 50% butyl alcohol under refluxing, each time for 45 minutes. The mixture was filtered and the filtrate was combined. The filtrate was charged into previously prepared D101 macroporous adsorbing resin, eluted with deionized water. The eluate was collected and concentrated, dried in vacuum oven at 60° C. to obtain *Codonopsis pilosula* extract, in which the content of *Codonopsis* extract was around 50% by weight.

Example 10

Preparation of Co-Extract of Peony and *Codonopsis*

Red peony powder (passed through 40-mesh screen) and raw powder of *Codonopsis* were taken in ratio by weight of 3:1, They were extracted twice with, based on the weight of the raw material, 10 folds by weight of water under refluxing, each time for 1 hour. The mixture was filtered and the extracted solution was combined. The extracted solution was charged into previously prepared D101 macroporous adsorbing resin, eluted with deionized water. The eluate was collected and concentrated, dried in vacuum oven at 60° C. to obtain the co-extract of red peony and *Codonopsis*, in which the content of Paeoniflorin is 75% by weight, and the content of *Codonopsis* extract is 25% by weight.

Example 11

Screening of the Medicines Against Foaming Damage of U937 Cells Caused By Oxidative Low Density Lipoprotein (ox-LDL)

The test medicines used in Example 11~14 listed as follows:
H1: Peony extract obtained from Example 1
H2: *Corydalis* (*Corydalis Tuber*) extract. The extracting method is as follows:
1 part by weight of corydalis powder was extracted 3 times with 6 parts by weight of 60% ethanol having pH adjusted to 4.5 with acetic acid under refluxing, each time for 1.5 hours. The extracted solution was combined and concentrated under reduced pressure to dryness. Approximate 600 ml water was added into the residue for dissolving. After filtering, the filtrate was charged into previously prepared D101 macroporous adsorbing resin, eluted with 40% ethanol, the eluate was discarded, eluted again with 95% ethanol, the eluate was collected and concentrated under reduced pressure, dried in vacuo to obtain the title substance.
H3: *Salvia* (*Salviae Miltiorrhizae Radix*) extract. The extracting method is as follows:
1 part by weight of salvia powder was soaked overnight with 10 parts by weight of water, and then extracted under refluxing for 30 minutes. The mixture was filtered, and the extracted under refluxing with 10 parts by weight of water for 2 hours. The filter solution was combined, cooled, and then adjusted pH to 2. The solution was extracted with absolute ethyl ether, the ethyl ether layer was collected and concentrated under reduced pressure, dried in vacuo to obtain the title substance.

H4: Tangkuei (*Angelicae Sinensis Radix*) extract. The extracting method is as follows:

1 part by weight of tangkuei powder was extracted 2 times with 6 parts by weight and 10 parts by weight of 70% ethanol respectively under refluxing, each time for 2 hours. The filtrates were combined and concentrated under reduced pressure until the absence of the alcoholic smell. 3 parts by weight of water were added thereto, the mixture was heated to dissolve at 50° C. and filtered. The filtrate was charged into previously prepared D101 macroporous adsorbing resin, eluted with water and 30% ethanol successively, the eluate was discarded, and then eluted again with 80% ethanol, the eluate was collected and concentrated in vacuo, dried in vacuo to obtain the title substance.

H5: *Ligusticum* (*Ligustici Rhizoma*) extract. The extracting method is as follows:

1 part by weight of ligusticum powder was extracted 3 times with 10 parts by weight of 95% ethanol under refluxing, each time for 2 hours. The filtrates were combined and concentrated under reduced pressure to dryness. Water was added to dissolve the residue at 50° C., the resulting solution was filtered and charged into previously prepared D101 macroporous adsorbing resin, eluted with water and 30% ethanol successively, the eluate was discarded, and then eluted again with 60% ethanol, the eluate was collected and concentrated under reduced pressure, dried in vacuo at 40° C. to obtain the title substance.

B1: *Codonopsis* Extract Obtained From Example 7

B2: Total Glucosides of *Astragalus* (*Astragali Radix*). The extracting method is as follows:

1 part by weight of astragalus powder was soaked with 10 parts by weight of 60% ethanol for 2 hours, and then extacted twice under refluxing, each for 2 hours. The filtrate was combined and concentrated until the absence of the alcoholic smell. Water was added to dissolve the residue, the resulting solution was filtered and charged into macroporous adsorbing resin, eluted with water and 40% ethanol successively, the eluate was discarded, and then eluted again with 80% ethanol, the eluate was collected and concentrated under reduced pressure to extract concrete, dried in vacuo to obtain the title substance.

HB: Preparation of HB in Example 14

*Codonopisis* (0.625 parts by weight), tangkuei (*Angelicae Sinensis Radix*), (1.0416 parts by weight), radix rehmanniae (0.2083 parts by weight), ligusticum (0.5208 parts by weight), red peony (0.2083 parts by weight), Salvia (0.3125 parts by weight), peach kernel (*Persicae Semen*) (0.2083 parts by weight), carthamus (*Carthami Flos*) (0.5208 parts by weight), cortex moutan (*Moutan Radicis Cortex*) (0.3125 parts by weight), areca husk (*Arecae Pericarpium*) (0.2083 parts by weight), scrophularia (*Scrophulariae Radix*) (0.4166 parts by weight), alisma (*Alismatis Rhizoma*) (0.4166 parts by weight), poria (0.5208 parts by weight), crataegus (*Crataegi Fructus*) (0.625 parts by weight) and licorice (*Glycyrrhizae Radix*) (0.1046 parts by weight) were mixed, the extraction was done in the presence of water as the extraction solvent, dried to obtain the title substance.

1. Object: To evaluate whether the medicine has a protecting effect on U937 cell by detection of the foaming damage (inhibition of cell growth) caused by ox-LDL(80 mg/ml) on the cultured U937 cell.

2. Materials and Method

U937 cell culture and treatment: The U937 cells were regularly cultured in RPMI-1640 culture medium supplemented with 10% FBS (containing 100 u/ml penicillin and 100 u/ml streptomycin respectively). And then, the U937 cells were placed into the incubator and incubated at 37° C., 5% $CO_2$ and 95% air, in which the cell density is about $1 \times 10^6$ unit/L. The medium was refreshed once every two days.

3. Experimental Method

The preparation of medicine-containing serum. 30 SD (Sprague-Dawley) female rats were emplyed with the average body weight of about 200 g. The animals were randomly divided into one control group (CK) and 9 test groups (H1B1, H1B2, H2B1, H2B2, H3B1, H4B1, H4B2, H5B1, H5B2, respectively), in which H1 is the peony extract obtained from Example 1, while B1 is the Codonopsis extract obtained from Example 4 7. The rats were administered the given amount of medicine by gastric perfusion (H extract 150 g/kg.BW, B extract 50 g/kg.BW) for 3 days continuously. At day 4, blood samples were collected from rats' abdominal aorta half an hour after the gastric perfusion administration. After centrifugated for 20 minutes at 4000 rpm, the supernatant was collected. The samples were stored at −20° C. in refrigerator for further use before activated 56° C. for 30 min.

The U937 cells were cultured for exponential grown, after which the cells were transferred into no serum RPMI-1640 culture medium and incubated for 24 hours, and the cell density was adjusted to $2 \times 10^5$ unit/ml with serum-free culture medium. The U937 cells were divided into normal control group (Group C), foam cell model group (Group M), control serum group (Group CS) and test group (Group drug). In Group C, the cells were incubated in serum-free RPMI-1640 culture medium. In Group M, the cells were incubated in serum-free RPMI-1640 culture medium supplemented with ox-LDL (the final concentration of ox-LDL was 80 mg·L). In Group CS, the cells were incubated in serum-free RPMI-1640 culture medium supplemented with control serum to the final concentration of 20% (the final concentration of ox-LDL is 80 mg·L). In Group drug, the cells were incubated in the serum-free RPMI-1640 culture medium supplemented with various medicines to the final concentration of 20% (the final concentration of ox-LDL is 80 mg·L). All groups above were incubated in 96-well microplates, 6 wells for each group. After incubated for 12 hours, the cells were collected and detected for proliferation activity (WST).

4. Result

Figure 1:
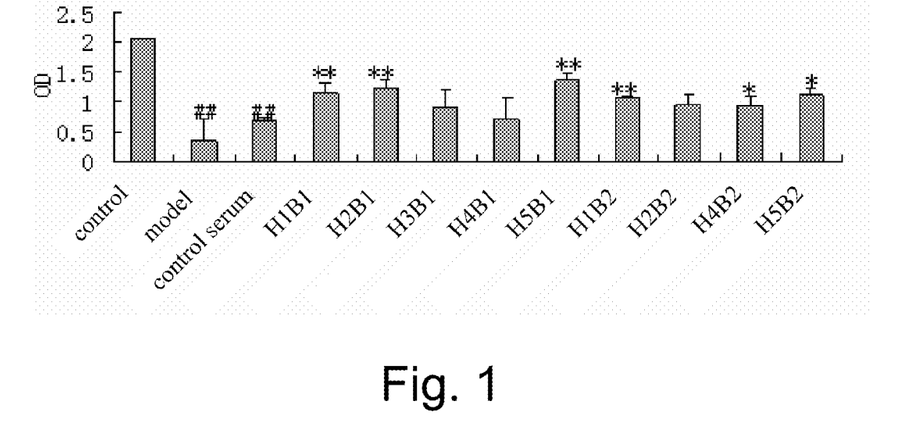
FIG. 1 shows the protecting effect on the medicine candidate against the foaming damage of U937 cells caused by ox-LDL. Remarks: *: $p<0.05$ vs control serum, **: $p<0.05$ vs control serum; ##: $p<0.05$ vs model.

As shown in Table 1 and FIG. 1, nine medicines were tested, in which 6 medicines had substantial effect against foaming damage of U937 cells caused by oxidant low density lipoprotein (ox-LDL) at the concentration of 20%, namely, H1B1, H2B1, H5B1, H1B2, H4B2 and H5B2. The other medicines were ineffective at the dose of 100 μg/ml.

TABLE 1

| H1B1 | H2B1 | H3B1 | H4B1 | H5B1 | H1B2 | H2B2 | H4B2 | H5B2 |
|------|------|------|------|------|------|------|------|------|
| ✓    | ✓    | •    | •    | ✓    | ✓    | •    | ✓    | ✓    |

✓: effective
•: ineffective

Example 12

Screening For Medicines With Protecting Effect Against Endothelial Cell Damage Caused By ox-LDL (1) Experimental Materials DMEM culture medium (Gibco), newborn calf serum (Hangzhou Sijiqin biotech company), oxidative low density lipoprotein (ox-LDL, Beijing Union Medical Preliminary College), Simvastatin (Hangzhou Merck CO. Ltd.), Wst-1 kit (Roche).

(2) Experimental Method

1. The preparation of medicine-containing serum. 30 SD (Sprague-Dawley) female rats were employed with the average body weight of about 200 g. The animals were randomly divided into one control group (CK) and 9 test groups (H1B1, H1B2, H2B1, H2B2, H3B1, H4B1, H4B2, H5B1, H5B2, respectively). The rats were administered the given amount of medicine each day by gastric perfusion (H extract 150 g/kg.BW, B extract 50 g/kg.BW) for 3 days continuously. At day 4, blood samples were collected from rats' abdominal aorta half an hour after the gastric perfusion administration. After centrifugated for 20 minutes at 4000 rpm, the supernatant was collected. The samples were stored at $-20°$ C. in refrigerator for further use before activated 56° C. for 30 min.

2. Experimental Grouping. The human umbilical vein vascular endothelial cells were incubated in 96-well microplates. The cells were divided into normal group (normal), model group (ox-LDL), serum groups (CK, H1B1, H1B2, H2B1, H2B2, H3B1, H4B1, H4B2, H5B1, H5B2) and positive control group (Sim), totally 13 groups, 6 wells for each group. For the normal group, 200 μl DMEM culture medium containing 20% newborn calf serum was added. For the other groups, 40 μl corresponding serum was added into the serum groups, while the positive control group was added 10 μl 200 μmol/ml simvastatin (final concentration 10 μmol/ml), and then complemented with DMEM culture medium containing 20% newborn calf serum to total volume of 200 μl. The cells were incubated at 37° C., 5% $CO_2$ for 24 hours.

3. The determination of cell metabolic activity. 20 μl WST-1 reagent was add into each well. After incubating the cells at 37° C., 5% $CO_2$ for 1.5 hr, the OD values were detected at 440 nm.

(3). Experimental Results

Figure 2:
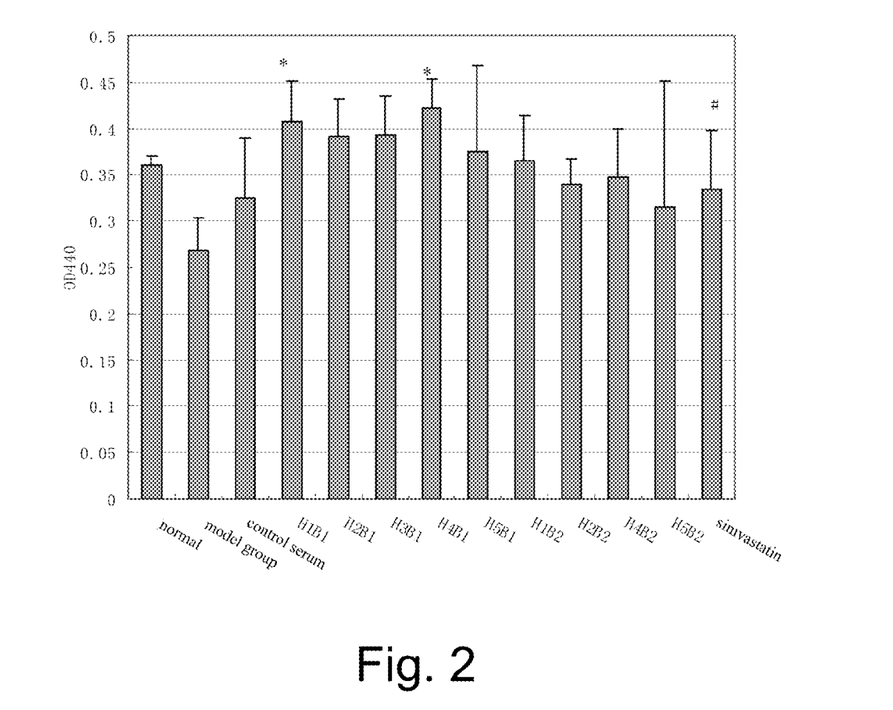
FIG. 2 shows the protecting effect on the medicine candidate against the damage of U937 endothelial cells caused by ox-LDL. Remarks: *: $p<0.05$ vs ck, **: $p<0.05$ vs ck; ##: $p<0.05$ vs ox-LDL.

As shown in FIG. 2, compared with the control serum groups, groups H1B1 and H4B can significantly improve the reduction of cell metabolic activity of human umbilical vein vascular endothelial cells caused by ox-LDL damage. The experimental data was summarized in table 2.

TABLE 2

| H1B1 | H2B1 | H3B1 | H4B1 | H5B1 | H1B2 | H2B2 | H4B2 | H5B2 |
|------|------|------|------|------|------|------|------|------|
| ✓ | • | • | ✓ | • | • | • | • | • |

✓: effective
•: ineffective

Example 13

Drug Screening By Means of Myocardial Cell Model

Experimental Object:

Myocardial hypertrophy is a critical phase of myocardial reconstruction that can occur in common diseases of cardiovascular system, e.g. hypertension. It is also a common pathology of arrhythmia, heart failure and other deceases. And therefore, myocardial hypertrophy becomes a critical indicator whether the heart function enters the decompensation period. Now the myocardial cell model is employed to carry out the preliminary screening of medicines.

Experimental Method:

1. The establishment of myocardial hypertrophy model. The primary cultured myocardial cells were inoculated into 96-well microplates and the media were refreshed every 24 hours. During the first 48 hours, BrdU0.1 mM was added to inhibit the proliferation of fibroblast. At hour $36^{th}$, low energy culture medium (0.4% FBS) was added and the cells were cultured another 48 hours. The cells were divided into test group, blank group, angiotensin (AngII) group, AngII+ACEI group and ANGII+medicine group, in which the final concentration of AngII is $10^{-6}$M. For the positive control, the final concentration of Anti is $10^{-6}$M. The medicine-containing serums contained H1B1, H1B2, H2B2, H3B1, H4B1, H4B2, H5B1, H5B2 and CK, respectively, which were labeled successively. The dose was 20%.

2. Determination of the Protein Level

The culture medium was sucked off, and the cells were carefully washed with PBS (pH 7.3) twice. 0.1 ml 0.25% trypsase was added per well to digest cell, incubated at 50° C. for 30 min. And then, 1% SDS was added for each well, incubated for 30 minutes to decompose cell. The protein level was determined according to the Bradford method, in which 1 ml dying reagent was added for each 100 ul cell lysate and maintained for 30 min. The measurement was carried out by the Microplate Spectrophotometer.

3. Statistical t Test: $P<0.05$ Means Substantial Difference of Statistical Significance.

Figure 3:
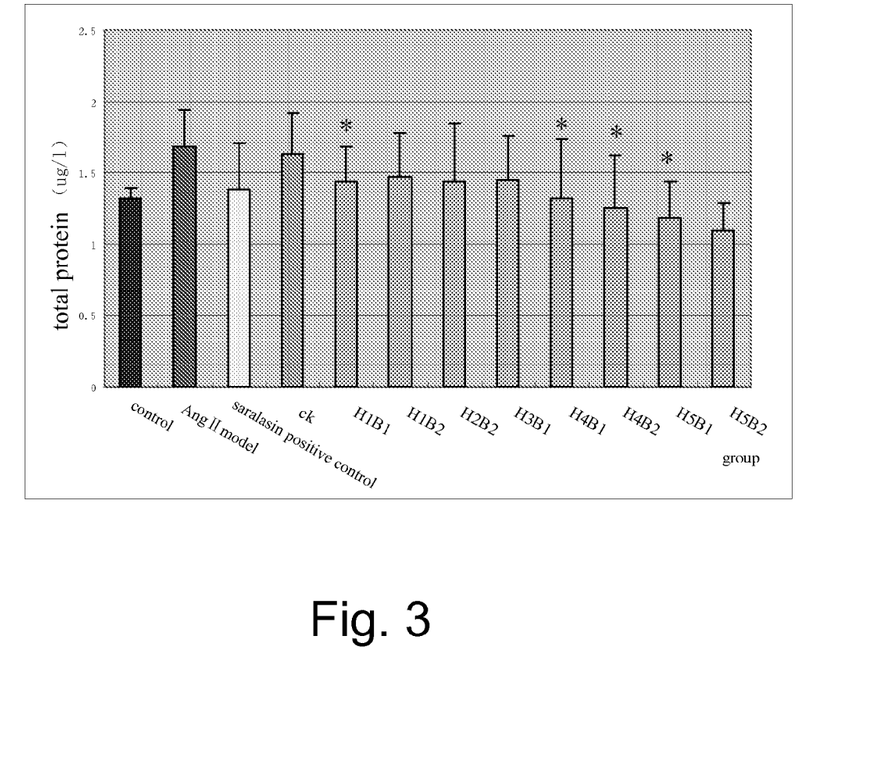
FIG. 3 shows the effect on the medicine candidate on the total protein content of myocardial cells.

Experimental results: see FIG. 3 and Table 3

TABLE 3

| Ck | H1B1 | H1B2 | H2B2 | H3B1 | H4B1 | H4B2 | H5B1 | H5B2 |
|----|------|------|------|------|------|------|------|------|
| • | ✓ | • | • | • | ✓ | ✓ | ✓ | • |

✓: effective
•: ineffective

Experimental Significance:

The size of myocardial cell was enlarged under the action of angiotensin II, the total protein level of cell was increased, the protein proliferation speeded up and the metabolic activity was enhanced. The total protein level in the myocardial cell could be used as the indicator to preliminarily evaluate whether there was a positive agonism or negative inhibition effect of the test medicines on myocardial cell growth.

The summary of the results of Examples 4~6 is shown in Table 4:

TABLE 4

| | H1B1 | H2B1 | H3B1 | H4B1 | H5B1 | H1B2 | H2B2 | H4B2 | H5B2 |
|---|---|---|---|---|---|---|---|---|---|
| Foam | ✓ | ✓ | • | • | ✓ | ✓ | • | ✓ | ✓ |
| Endothelial | ✓ | • | • | ✓ | • | • | • | • | • |
| Myocardial | ✓ | • | • | ✓ | ✓ | • | • | ✓ | • |

✓: effective
•: ineffective

According to the result, H1B1 was effective in all three models, while H4B1, H4B2 and H5B1 were effective in two models. And therefore, further study was done for H1B1.

Example 14

Screening for Hypolipidemic Medicines

1 Materials and Equipments
1.1 Test Medicines

As described before, the test medicine is the mixture of H series and B series in the ratio H:B (3:1). Recommended dose (for animal) is: H series: 150 mg/kg, B series: 50 mg/kg. HB is a separate mixture and the recommended does is 200 mg/kg.

Test medicine 1: H1+B1, ig 0.2 ml/10 g;
Test medicine 2: H2+B1, ig 0.2 ml/10 g;
Test medicine 3: H3+B1, ig 0.2 ml/10 g;
Test medicine 4: H4+B1, ig 0.2 ml/10 g;
Test medicine 5: H5+B1, ig 0.2 ml/10 g;
Test medicine 6: H1+B2, ig 0.2 ml/10 g;
Test medicine 7: H2+B2, ig 0.2 ml/10 g;
Test medicine 8: H3+B2, ig 0.2 ml/10 g;
Test medicine 9: H4+B2, ig 0.2 ml/10 g;
Test medicine 10: H5+B2, ig 0.2 ml/10 g;
Test medicine 11: HB ig 0.2 ml/10 g.

1.2 Experimental Animal

130 SPF ICR mice were employed with the body weight 20±2 g, half are male and the other half are female. Provided by Zhejiang Province Experimental Animal Center, Licence: SCXK(ZHE)2003-0001

1.3 Medicine and Reagent

Zocor (Hangzhou Merck CO. Ltd., batch S1059), 20 mg/kg, ig 0.2 ml/10 g was administered to mice;

Physiological Saline (Zhejiang Pinghu SapAce Pharmaceutics CO. Ltd., batch 041113-2);

Triglyceride kit (Shanghai Fuxing Changzheng Medical Science CO. Ltd., batch 2230060);

Cholesterol kit (Shanghai Fuxing Changzheng Medical Science CO. Ltd., batch 1300060);

High density lipoproteincholesterol kit (Witamann Biotech Nanjing CO. Ltd., batch BD2228);

1.4 Equipment

LP123 Model electronic balance; SE full automatic biochemical analyzer; GL-20G-II refrigerated high speed centrifuge.

2. Experimental Method 2.1 Production of 75% yolk emulsion (Xu Shuyun et al., "Pharmacological Experimental Method (3rd edition) Beijing People's Medical Publishing House, 2002; 1201~1203)

90 ml yolk and 30 ml physiological Saline were mixed thoroughly in electric mixer to form emulsion, which was stored at 4° C. for further use.

2.2 Lipid Lowering Screening Test

140 ICR mice were randomly divided into 14 groups: test medicine 1, test medicine 2, test medicine 3, test medicine 4, test medicine 5, test medicine 6, test medicine 7, test medicine 8, test medicine 9, test medicine 10, test medicine 11, postive control group (Zocor), model control group and normal control group, 10 mice for each group, half male and half female. Once daily for a continous 7-day period, the model control group and normal control group were provided with same volume of distilled water, while the other groups were administered with medicines by gastric perfusion. 2 hours after the last gastric perfusion, except of the normal control group, fresh yolk emulsion was intraperitoneally injected to the rest 13 groups of mice, 0.5 ml for a single animal. After 20 hours, eye ball was plucked and blood was collected, make sure 12 hours fasting before the collection. The content of total cholesterol (TC), triglyceride (TG) and high density lipoprotein (HDL-C) of the serum were measured.

2.3 Statistical Assay

EXCEL was employed to analyze the significant difference between the groups. The result is shown in X±SD.

3 Results 3.1 Effect on Total Serum Cholesterol of Hyperlipidemia Mice (Table 5)

According to Table 5, compared with normal control group, model control group has higher TC with significant difference (P<0.01), which means the success of the hyperlipidemia mice modeling. Compared with model control group, test medicine 1 and test medicine 3 have lower TC with significant difference (P<0.05), which means test medicine 1 and test medicine 3 can inhibit the increasing total serum cholesterol of hyperlipidemia mice.

TABLE 5 total serum cholesterol (TC) content

| Group | animal number | Dose (mg/kg) | TC (mmol/L) |
|---|---|---|---|
| normal control group | 10 | — | 3.51 ± 0.67 |
| model control group | 10 | — | 11.63 ± 2.94△△ |
| test medicine 1 | 10 | 200 | 8.03 ± 4.06* |
| test medicine 2 | 10 | 200 | 10.31 ± 5.32 |
| test medicine 3 | 10 | 200 | 8.62 ± 4.36* |
| test medicine 4 | 10 | 200 | 11.45 ± 6.18 |
| test medicine 5 | 10 | 200 | 11.94 ± 8.09 |
| test medicine 6 | 10 | 200 | 9.53 ± 6.77 |
| test medicine 7 | 10 | 200 | 9.89 ± 5.77 |
| test medicine 8 | 10 | 200 | 13.27 ± 5.98 |
| test medicine 9 | 10 | 200 | 11.79 ± 4.64 |
| test medicine 10 | 10 | 200 | 12.22 ± 5.07 |
| test medicine 11 | 10 | 200 | 11.22 ± 4.57 |
| positive control group | 10 | 20 | 8.58 ± 4.18* |

Note:
compared with normal control group, $^{\triangle}P < 0.05$, $^{\triangle\triangle}P < 0.01$;
Compared with model control group, $*P < 0.05$, $**P < 0.01$;

3.2 Effect on Serum Triglyceride of Hyperlipidemia Mice (Table 6)

TABLE 6 serum triglyceride (TG) content

| Group | animal number | dose (mg/kg) | TG (mmol/L) |
|---|---|---|---|
| normal control group | 10 | — | 1.15 ± 0.29 |
| model control group | 10 | — | 12.81 ± 5.22$^{\Delta\Delta}$ |
| test medicine 1 | 10 | 200 | 7.98 ± 4.89* |
| test medicine 2 | 10 | 200 | 9.25 ± 6.15 |
| test medicine 3 | 10 | 200 | 8.86 ± 5.45 |
| test medicine 4 | 10 | 200 | 11.35 ± 5.96 |
| test medicine 5 | 10 | 200 | 9.85 ± 6.50 |
| test medicine 6 | 10 | 200 | 7.28 ± 5.90* |
| test medicine 7 | 10 | 200 | 8.64 ± 5.94 |
| test medicine 8 | 10 | 200 | 12.34 ± 5.67 |
| test medicine 9 | 10 | 200 | 12.70 ± 5.40 |
| test medicine 10 | 10 | 200 | 12.79 ± 5.60 |
| test medicine 11 | 10 | 200 | 10.98 ± 5.76 |
| positive control group | 10 | 20 | 7.78 ± 5.36* |

Note:
compared with normal control group, $^{\Delta}P < 0.05$, $^{\Delta\Delta}P < 0.01$;
Compared with model control group, *P < 0.05, **P < 0.01;

According to Table 6, compared with normal control group, model control group has higher TG with significant difference (P<0.01), which means the success of the hyperlipidemia mice modeling. Compared with model control group, test medicine 1 and test medicine 6 have lower TG with significant difference (P<0.05); test medicine 3 and test medicine 7 show a trend of decreasing but with no statistical significance. This result shows medicine 1 and medicine 6 can inhibit the increasing serum triglyceride of hyperlipidemia mice.

3.3 Effect on Serum High Density Lipoproteincholesterol (HDL-C) of Hyperlipidemia Mice (Table 7)

TABLE 7

Serum high density lipoproteincholesterol (HDL-C) content

| Group | animal number | dose (mg/kg) | HDL-C (mmol/L) | HDL-C/TC |
|---|---|---|---|---|
| normal control group | 10 | — | 1.67 ± 0.18 | 0.48 ± 0.06 |
| model control group | 10 | — | 2.37 ± 0.27 | 0.22 ± 0.06$^{\Delta\Delta}$ |
| test medicine 1 | 10 | 200 | 2.08 ± 0.33 | 0.30 ± 0.09* |
| test medicine 2 | 10 | 200 | 2.34 ± 0.31 | 0.28 ± 0.11 |
| test medicine 3 | 10 | 200 | 2.21 ± 0.27 | 0.30 ± 0.10* |
| test medicine 4 | 10 | 200 | 2.40 ± 0.32 | 0.27 ± 0.13 |
| test medicine 5 | 10 | 200 | 2.35 ± 0.37 | 0.29 ± 0.16 |
| test medicine 6 | 10 | 200 | 2.14 ± 0.36 | 0.30 ± 0.13 |
| test medicine 7 | 10 | 200 | 2.34 ± 0.24 | 0.30 ± 0.12 |
| test medicine 8 | 10 | 200 | 2.61 ± 0.27 | 0.23 ± 0.09 |
| test medicine 9 | 10 | 200 | 2.56 ± 0.28 | 0.25 ± 0.10 |
| test medicine 10 | 10 | 200 | 2.50 ± 0.23 | 0.24 ± 0.11 |
| test medicine 11 | 10 | 200 | 2.54 ± 0.26 | 0.25 ± 0.10 |
| positive control group | 10 | 20 | 1.39 ± 0.23 | 0.18 ± 0.05 |

Note:
compared with normal control group, $^{\Delta}P < 0.05$, $^{\Delta\Delta}P < 0.01$;
Compared with model control group, *P < 0.05, **P < 0.01;

According to Table 7, compared with normal control group, model control group has lower HDL-C/TC ratio, with significant difference (P<0.01). Compared with model control group, test medicine 1 and test medicine 3 have higher HDL-C/TC ratio, with significant difference (P<0.05); test medicine 6 and test medicine 7 show a trend of increasing of HDL-C/TC ratio, but without statistical significance.

4 Conclusion

The hypolipidemic medicines, also called blood lipid-adjusting medicines, are a series of medicines that can adjust lipid metabolism and can lower overhigh serum TC or TG and/or increase overlow serum HDL-C to improve blood lipid situation. The hypolipidemic medicines, according to their efficacy, can be categorized into 2 groups: the group with a primary effect of TC lowering and a subordinate effect of TG lowering; as well as the group with a primary effect of TG lowering and a subordinate effect of TC lowering. Few medicines can selectively lower TC or TG (Wang Haiyong et al., "The development of hypolipidemic medicine", *Foreign Medical, Pharmacy fascicule*, 2004, 31(3): 160~166).

The above results show the following results: test medicine 1 and test medicine 3 can inhibit the increase of total serum cholesterol (TC) in hyperlipidemia mice; test medicine 1 and test medicine 6 can inhibit the increase of serum triglyceride (TG) in hyperlipidemia mice, while test medicine 3 and test medicine 7 show a trend of decreasing of serum triglyceride (TG) in hyperlipidemia mice; test medicine 1 and test medicine 3 can increase the HDL-C/TC ratio, while test medicine 6 and test medicine 7 show a trend of increasing the HDL-C/TC ratio.

In summary, test medicine 1 can simultaneously decrease TC and TG, and increase HDL-C/TC ratio. Test medicine 3 can decrease TC, increase HDL-C/TC ratio, and has a trend of decreasing TG. Test medicine 6 can decrease TG, and has a trend of increasing HDL-C/TC ratio. Test medicine 7 has trends of decreasing TG and increasing HDL-C/TC ratio.

Conclusion: Test Medicine 1 has a Better Hypolipidemic Effect.

Example 15

Hypolipidemic Effect

1. Materials and Equipments 1.1 Experimental Medicines.

H1-1 is the peony extract obtained from Example 1 (the total content of glucosides of red peony is 60%), H1-2 is the peony extract obtained from Example 2 (the total content of glucosides of red peony is 90%), H1-3 is the peony extract obtained from Example 3 (the total content of penoniflorin is 50%), B1-1 is the *Codonopsis* extract obtained from Example 7 (the content of Codonopsis extract is 90%), B1-2 is the *Codonopsis* extract obtained from Example 8 (the *Codonopsis pilosula* extract extract content is 60%), B1-3 is the *Codonopsis* extract obtained from Example 9 (the content of *Codonopsis* extract is 50%), H1B1 is the co-extract of red peony and *Codonopsis* from Example 10 (the content of penoniflorin is 75% and the content of *Codonopsis* extract extract content is 25%). Group H1 and B1 were mixed in different ratios (see Table 8) and formulated into different test medicines.

Recommended dose (animal): H1+B1=200 mg/kg body weight, ig dose is 0.2 ml/10 g body weight.

TABLE 8 dose of test medicines

| Group | H1-1 (mg) | B1-1 (mg) | H1-2 (mg) | B1-2 (mg) | H1-3 (mg) | B1-3 (mg) | H1B1 (mg) | Weight ratio of Paeonia extract and Codonopsis pilosula extract |
|---|---|---|---|---|---|---|---|---|
| test medicine 1 | 0 | 200 | — | — | — | — | — | |
| test medicine 2 | 50 | 150 | — | — | — | — | — | 0.2:1 |
| test medicine 3 | 100 | 100 | — | — | — | — | — | 0.7:1 |
| test medicine 4 | 150 | 50 | — | — | — | — | — | 2:1 |
| test medicine 5 | 160 | 40 | — | — | — | — | — | 2.7:1 |
| test medicine 6 | 170 | 30 | — | — | — | — | — | 3.7:1 |
| test medicine 7 | 180 | 20 | — | — | — | — | — | 6:1 |
| test medicine 8 | 190 | 10 | — | — | — | — | — | 12.7:1 |
| test medicine 9 | 200 | 0 | — | — | — | — | — | |
| test medicine 10 | — | — | 0 | 200 | — | — | — | |
| test medicine 11 | — | — | 50 | 150 | — | — | — | 0.5:1 |
| test medicine 12 | — | — | 100 | 100 | — | — | — | 1.5:1 |
| test medicine 13 | — | — | 150 | 50 | — | — | — | 4.5:1 |
| test medicine 14 | — | — | 180 | 20 | | | | 13.5:1 |
| test medicine 15 | — | — | 190 | 10 | | | | 28.5:1 |
| test medicine 16 | — | — | 200 | 0 | — | — | — | |
| test medicine 17 | — | — | — | — | 0 | 200 | — | |
| test medicine 18 | — | — | — | — | 50 | 150 | — | 0.3:1 |
| test medicine 19 | — | — | — | — | 100 | 100 | — | 1:1 |
| test medicine 20 | — | — | — | — | 150 | 50 | — | 3:1 |
| test medicine 21 | | | | | 190 | 10 | | 19:1 |
| test medicine 22 | | | | | 200 | 0 | | |
| test medicine 23 | — | — | — | — | — | — | 200 | 3:1 |

1.2. Experimental Animal

100 SPF ICR mice were employed with the body weight 20±2 g, half are male and the other half are female. Provided by Zhejiang Province Experimental Animal Center, Licence: SCXK(ZHE)2003-0001

1.3 Medicine and Reagent

Zocor (Hangzhou Merck co. Ltd., batch S1059), 20 mg/kg, ig 0.2 ml/10 g was administered to mice;

Physiological Saline (Zhejiang Pinghu SapAce Pharmaceutics CO. Ltd., batch 041113-2);

Triglyceride kit (Shanghai Fuxing Changzheng Medical CO. Ltd., batch 2230060);

Cholesterol kit (Shanghai Fuxing Changzheng Medical CO. Ltd., batch 1300060);

High density lipoproteincholesterol test kit (Witamann Biotech Nanjing co. Ltd., batch BD2228);

1.4 Equipment

LP123 Model electronic balance; SE full automatic biochemical analyzer; GL-20G-II refrigerated high speed centrifuge.

2. Experimental Method 2.1 Production of 75% Yolk Emulsion 90 ml yolk and 30 ml physiological Saline were mixed thoroughly in electric mixer to form emulsion, which was stored at 4° C. for further use.

2.2 Lipid Lowering Screening Test

230 ICR mice were randomly divided into 23 groups: test medicine 1-23 groups, postive control group (Zocor), model control group and normal control group, 10 mice for each group, half male and half female. Once daily for a continous 7-day period, the model control group and normal control group were provided with same volume of distilled water, while the other groups were administered with medicines by gastric perfusion. 2 hours after the last gastric perfusion, except for the normal control group, fresh yolk emulsion was intraperitoneally injected to the rest 22 groups of mice, 0.5 ml for a single animal. After 20 hours, eye ball was plucked and blood was collected, make sure 12 hours fasting before the collection. The content of total cholesterol (TC), triglyceride (TG) and high density lipoprotein (HDL-C) of the serum were measured.

2.3 Statistical Assay

T test was employed to analyze the significant difference between the groups. The result is shown in X±SD.

3 Results 3.1 Effect on Total Serum Cholesterol of Hyperlipidemia Mice (Table 9)

TABLE 9 total serum cholesterol (TC) content

| Group | animal number | dose (mg/kg) | TC (mmol/L) |
|---|---|---|---|
| normal control group | 10 | — | 3.42 ± 0.49 |
| model control group | 10 | — | 11.26 ± 4.58$^{\triangle\triangle}$ |
| test medicine 1 | 10 | 200 | 10.97 ± 4.52 |
| test medicine 2 | 10 | 200 | 9.83 ± 4.24 |
| test medicine 3 | 10 | 200 | 8.63 ± 2.77* |
| test medicine 4 | 10 | 200 | 7.73 ± 3.46* |
| test medicine 5 | 10 | 200 | 8.53 ± 3.57* |
| test medicine 6 | 10 | 200 | 6.72 ± 2.99** |
| test medicine 7 | 10 | 200 | 8.73 ± 2.88* |
| test medicine 8 | 10 | 200 | 8.93 ± 3.75* |
| test medicine 9 | 10 | 200 | 10.77 ± 5.52 |
| test medicine 10 | 10 | 200 | 11.02 ± 4.32 |
| test medicine 11 | 10 | 200 | 8.73 ± 4.56* |
| test medicine 12 | 10 | 200 | 8.23 ± 3.88* |
| test medicine 13 | 10 | 200 | 6.84 ± 3.79** |
| test medicine 14 | 10 | 200 | 8.93 ± 4.47* |
| test medicine 15 | 10 | 200 | 11.57 ± 4.82 |
| test medicine 16 | 10 | 200 | 10.68 ± 4.47 |
| test medicine 17 | 10 | 200 | 11.87 ± 5.62 |
| test medicine 18 | 10 | 200 | 10.97 ± 5.82 |
| test medicine 19 | 10 | 200 | 8.53 ± 4.45* |
| test medicine 20 | 10 | 200 | 8.23 ± 4.57* |
| test medicine 21 | 10 | 200 | 8.67 ± 4.42* |
| test medicine 22 | 10 | 200 | 10.89 ± 5.67 |
| test medicine 23 | 10 | 200 | 11.77 ± 4.82 |
| positive control group | 10 | 20 | 8.03 ± 3.12* |

Note:
compared with normal control group, $^{\triangle}$P < 0.05, $^{\triangle\triangle}$P < 0.01;
Compared with model control group, *P < 0.05, **P < 0.01;

According to Table 9, compared with normal control group, model control group has higher TC, with significant difference (P<0.01), which means the success of the hyperlipidemia mice modeling. Compared with model control group, the test medicine 3, 4, 5, 7, 8, 11, 12, 14, 19, 20, 21 and positive control groups have lower TC, with significant difference (P<0.05). Medicine 6 and 13 have lower TC with substantially significant difference (P<0.01). The results show that the above medicines can inhibit the increase total serum cholesterol in hyperlipidemia mice.

3.2. Effect on Serum Triglyceride of Hyperlipidemia Mice (Table 10)

TABLE 10 serum triglyceride (TG) content

| Group | animal number | dose (mg/kg) | TG (mmol/L) |
|---|---|---|---|
| normal control group | 10 | — | 0.85 ± 0.52 |
| model control group | 10 | — | 12.68 ± 5.27$^{\triangle\triangle}$ |
| test medicine 1 | 10 | 200 | 12.78 ± 5.23 |
| test medicine 2 | 10 | 200 | 10.75 ± 5.54 |
| test medicine 3 | 10 | 200 | 8.98 ± 3.18* |
| test medicine 4 | 10 | 200 | 8.78 ± 4.68* |
| test medicine 5 | 10 | 200 | 8.69 ± 4.37* |
| test medicine 6 | 10 | 200 | 8.79 ± 3.79* |
| test medicine 7 | 10 | 200 | 8.97 ± 4.57* |
| test medicine 8 | 10 | 200 | 9.11 ± 4.32* |
| test medicine 9 | 10 | 200 | 10.68 ± 5.35 |
| test medicine 10 | 10 | 200 | 12.11 ± 5.27 |
| test medicine 11 | 10 | 200 | 9.15 ± 4.28* |
| test medicine 12 | 10 | 200 | 9.04 ± 4.72* |
| test medicine 13 | 10 | 200 | 8.68 ± 3.86* |
| test medicine 14 | 10 | 200 | 9.11 ± 5.11* |
| test medicine 15 | 10 | 200 | 12.67 ± 4.35 |
| test medicine 16 | 10 | 200 | 10.57 ± 5.23 |
| test medicine 17 | 10 | 200 | 11.64 ± 5.34 |
| test medicine 18 | 10 | 200 | 10.32 ± 4.26 |
| test medicine 19 | 10 | 200 | 8.89 ± 4.54* |
| test medicine 20 | 10 | 200 | 8.93 ± 4.47* |
| test medicine 21 | 10 | 200 | 9.08 ± 4.55* |
| test medicine 22 | 10 | 200 | 11.88 ± 5.22 |
| test medicine 23 | 10 | 200 | 10.34 ± 5.28 |
| positive control group | 10 | 20 | 8.57 ± 4.20* |

Note:
compared with normal control group, $^{\triangle}$P < 0.05, $^{\triangle\triangle}$P < 0.01;
Compared with model control group, *P < 0.05, **P < 0.01;

According to Table 10, compared with normal control group, model control group has higher TG, with significant difference (P<0.01), which means the success of the hyperlipidemia mice modeling. Compared with model control group, medicine 3, 4, 5, 6, 7, 8, 11, 12, 13, 14, 19, 20, 21 and positive control groups have lower TG, with significant difference (P<0.05), which means the above medicines can inhibit the increase of serum triglyceride in hyperlipidemia mice.

3.3 Effect on Serum High Density Lipoproteincholesterol (HDL-C) of Hyperlipidemia Mice (Table 11)

TABLE 11

Serum high density lipoproteincholesterol (HDL-C) content

| Group | animal number | dose (mg/kg) | HDL-C (mmol/L) | HDL-C/TC |
|---|---|---|---|---|
| normal control group | 10 | — | 1.36 ± 0.14 | 0.40 ± 0.04 |
| model control group | 10 | — | 1.71 ± 0.15 | 0.18 ± 0.07$^{\triangle\triangle}$ |
| test medicine 1 | 10 | 200 | 1.89 ± 0.12 | 0.22 ± 0.10 |
| test medicine 2 | 10 | 200 | 1.67 ± 0.15 | 0.20 ± 0.08 |
| test medicine 3 | 10 | 200 | 1.65 ± 0.08 | 0.24 ± 0.10* |
| test medicine 4 | 10 | 200 | 1.62 ± 0.12 | 0.26 ± 0.08* |
| test medicine 5 | 10 | 200 | 1.64 ± 0.16 | 0.28 ± 0.09** |
| test medicine 6 | 10 | 200 | 1.85 ± 0.11 | 0.25 ± 0.08* |
| test medicine 7 | 10 | 200 | 1.86 ± 0.08 | 0.24 ± 0.07* |
| test medicine 8 | 10 | 200 | 1.72 ± 0.12 | 0.24 ± 0.10* |
| test medicine 9 | 10 | 200 | 1.82 ± 0.13 | 0.19 ± 0.10 |
| test medicine 10 | 10 | 200 | 1.86 ± 0.14 | 0.20 ± 0.10 |
| test medicine 11 | 10 | 200 | 1.68 ± 0.13 | 0.24 ± 0.09* |
| test medicine 12 | 10 | 200 | 1.65 ± 0.15 | 0.24 ± 0.08* |
| test medicine 13 | 10 | 200 | 1.62 ± 0.09 | 0.26 ± 0.10* |
| test medicine 14 | 10 | 200 | 1.82 ± 0.15 | 0.24 ± 0.10* |
| test medicine 15 | 10 | 200 | 1.87 ± 0.13 | 0.20 ± 0.09 |
| test medicine 16 | 10 | 200 | 1.71 ± 0.16 | 0.20 ± 0.07 |
| test medicine 17 | 10 | 200 | 1.69 ± 0.13 | 0.20 ± 0.07 |

TABLE 11-continued

Serum high density lipoproteincholesterol (HDL-C) content

| Group | animal number | dose (mg/kg) | HDL-C (mmol/L) | HDL-C/TC |
|---|---|---|---|---|
| test medicine 18 | 10 | 200 | 1.64 ± 0.10 | 0.20 ± 0.08 |
| test medicine 19 | 10 | 200 | 1.84 ± 0.14 | 0.26 ± 0.10* |
| test medicine 20 | 10 | 200 | 1.65 ± 0.12 | 0.27 ± 0.07** |
| test medicine 21 | 10 | 200 | | 0.24 ± 0.08* |
| test medicine 22 | 10 | 200 | | 0.19 ± 0.10 |
| test medicine 23 | 10 | 200 | | 0.20 ± 0.08 |
| positive control group | 10 | 20 | 1.59 ± 0.13 | 0.22 ± 0.08 |

Note:
compared with normal control group, $^{\Delta}P < 0.05$, $^{\Delta\Delta}P < 0.01$;
Compared with model control group, *P < 0.05, **P < 0.01;

According to Table 11, compared with normal control group, model control group has lower HDL-C/TC ratio, with significant difference (P<0.01). Compared with model control group, the test medicine 3, 4, 5, 6, 7, 8, 11, 12, 13, 14, 19, 20, 21 groups have higher HDL-C/TC, with significant difference (P<0.05).

4. Conclusion

The hypolipidemic medicines can improve blood lipid condition mainly by lowering overhigh serum TC or TG and/or increasing overlow serum HDL-C. The hypolipidemic medicines, according to their efficacy, can be categorized into 2 groups: the group with a primary effect of TC lowering and a subordinate effect of TG lowering; as well as the group with a primary effect of TG lowering and a subordinate effect of TC lowering. A few medicines can selectively lower TC or TG.

The experimental data shows that most of the test medicines can simultaneously decrease TC and TG, and increase HDL-C/TC ratio.

Conclusion: most of the test medicines have certain hypolipidemic effect.

Example 16

Screening Test for Hypolipidemic Medicines

1 Material and Equipment
1.1 Experimental Medicines

H1 is peony extract obtained from Example 1. B1 is *Codonopsis* extract obtained from Example 7. The test medicines are mixtures of H1 and B1 with the ratio of 4:1 (the weight ratio of peony extract and Codonopsis extract is 2.7:1). The dose is listed in Table 12, ig 0.2 ml/10 g.

TABLE 12 the dose of the experimental medicine s

| Group | Dose H1 + B1 (mg/kg) |
|---|---|
| test medicine 1 | 50 |
| test medicine 2 | 100 |
| test medicine 3 | 200 |
| test medicine 4 | 400 |
| test medicine 5 | 800 |

1.2 Experimental Animals

80 SPF ICR mice were employed with the body weight 20±2 g, half are male and the other half are female. Provided by Zhejiang Province Experimental Animal Center, Licence: SCXK(ZHE)2003-0001

1.3 Medicine and Reagent

Zocor (Hangzhou Merck CO. Ltd., batch S1059), 20 mg/kg, ig 0.2 ml/10 g was administered to mice;

Physiological Saline (Zhang Jiagang Pharmaceutical Factory, batch 05101503);

Triglyceride kit (Shanghai Fuxing Changzheng Medical CO. Ltd., batch 2230060);

Cholesterol kit (Shanghai Fuxing Changzheng Medical CO. Ltd., batch 1300060);

High density lipoproteincholesterol test kit (Witamann Biotech Nanjing co. Ltd., batch BD2228);

1.4 Equipment

LP123 Model electronic balance; SE full automatic biochemical analyzer; GL-20G-II refrigerated high speed centrifuge.

2. Experimental Method
2.1 Production of 75% Yolk Emulsion 90 ml yolk and 30 ml physiological Saline were mixed thoroughly in electric mixer to form emulsion, which was stored at 4° C. for further use.

2.2 Test for Screen Hypolipidemic Medicines

80 ICR mice were randomly divided into 8 groups: test medicine 1, test medicine 2, test medicine 3, test medicine 4, test medicine 5, postive control group (Zocor), model control group and normal control group, 10 mice for each group, half male and half female. Once daily for a continuous 7-day period, the model control group and normal control group were provided with same volume of distilled water, while the other groups were administered with medicines by gastric perfusion. 2 hours after the last gastric perfusion, except for the normal control group, fresh yolk emulsion was intraperitoneally injected to the rest 7 groups of mice, 0.5 ml for a single animal. After 20 hours, eye ball was plucked and blood was collected, make sure 12 hours fasting before the collection. The content of total cholesterol (TC), triglyceride (TG) and high density lipoprotein (HDL-C) of the serum were measured.

2.3 Statistical Assay

T test was employed to analyze the significant difference between the groups. The result is shown in X±SD.

3 Results 3.1 Effect on Total Serum Cholesterol of Hyperlipidemia Mice (Table 13)

TABLE 13 total serum cholesterol (TC) content

| Group | animal number | dose (mg/kg) | TC (mmol/L) |
|---|---|---|---|
| normal control group | 10 | — | 3.59 ± 0.65 |
| model control group | 10 | — | 8.54 ± 4.30$^{\Delta\Delta}$ |
| test medicine 1 | 10 | 50 | 8.14 ± 3.17 |
| test medicine 2 | 10 | 100 | 5.62 ± 1.67* |
| test medicine 3 | 10 | 200 | 5.41 ± 1.62* |
| test medicine 4 | 10 | 400 | 5.57 ± 1.57* |
| test medicine 5 | 10 | 800 | 5.19 ± 1.82* |
| positive control group | 10 | 20 | 5.97 ± 2.40* |

Note:
compared with normal control group, $^{\Delta}P < 0.05$, $^{\Delta\Delta}P < 0.01$;
Compared with model control group, *P < 0.05, **P < 0.01;

According to Table 13, compared with normal control group, model control group has higher TC, with significant difference (P<0.01), which means the success of the hyperlipidemia mice modeling. Compared with model control group, medicine 2, 3, 4 and 5 groups have lower TC with significant difference (P<0.05), which shows that 100, 200, 400, 800 mg/kg dose of these medicines administered by gastric perfusion can all inhibit the increase of total serum cholesterol in hyperlipidemia mice.

3.2. Effect on Serum Triglyceride of Hyperlipidemia Mice (Table 14)

TABLE 14 serum triglyceride (TG) content

| Group | animal number | dose (mg/kg) | TG (mmol/L) |
|---|---|---|---|
| normal control group | 10 | — | 0.97 ± 0.24 |
| model control group | 10 | — | 8.89 ± 7.70$^{\Delta\Delta}$ |
| test medicine 1 | 10 | 50 | 5.62 ± 3.85 |
| test medicine 2 | 10 | 100 | 4.24 ± 3.06* |
| test medicine 3 | 10 | 200 | 4.30 ± 2.60* |
| test medicine 4 | 10 | 400 | 3.99 ± 2.56* |
| test medicine 5 | 10 | 800 | 3.67 ± 2.68* |
| positive control group | 10 | 20 | 4.31 ± 3.28* |

Note:
compared with normal control group, $^{\Delta}$P < 0.05, $^{\Delta\Delta}$P < 0.01;
Compared with model control group, *P < 0.05, **P < 0.01;

According to Table 14, compared with normal control group, model control group has higher TG, with significant difference (P<0.01), which means the success of the hyperlipidemia mice modeling. Compared with model control group, medicine 3, 4 and 5 groups have lower TG, with significant difference (P<0.05), which shows that all of 100, 200, 400, 800 mg/kg dose of these medicines administered by gastric perfusion can inhibit the increase serum triglyceride in hyperlipidemia mice.

3.3 Effect on Serum High Density Lipoproteincholesterol (HDL-C) of Hyperlipidemia Mice (Table 15)

TABLE 15

Serum high density lipoproteincholesterol (HDL-C) content

| Group | animal number | dose (mg/kg) | HDL-C (mmol/L) | HDL-C/TC |
|---|---|---|---|---|
| normal control group | 10 | — | 1.17 ± 0.11 | 0.33 ± 0.04 |
| model control group | 10 | — | 1.40 ± 0.15 | 0.21 ± 0.08$^{\Delta\Delta}$ |
| test medicine 1 | 10 | 50 | 1.44 ± 0.08 | 0.19 ± 0.05 |
| test medicine 2 | 10 | 100 | 1.34 ± 0.14 | 0.25 ± 0.06* |
| test medicine 3 | 10 | 200 | 1.35 ± 0.12 | 0.26 ± 0.05* |
| test medicine 4 | 10 | 400 | 1.34 ± 0.11 | 0.25 ± 0.05* |
| test medicine 5 | 10 | 800 | 1.30 ± 0.15 | 0.27 ± 0.06* |
| positive control group | 10 | 20 | 1.35 ± 0.15 | 0.26 ± 0.06* |

Note:
compared with normal control group, $^{\Delta}$P < 0.05, $^{\Delta\Delta}$P < 0.01;
Compared with model control group, *P < 0.05, **P < 0.01;

According to Table 15, compared with normal control group, model control group has lower HDL-C/TC ratio, with significant difference (P<0.01). Compared with model control group, medicine 2, 3, 4 and 5 groups have higher HDL-C/TC, with significant difference (P<0.05). It shows that all of 100, 200, 400, 800 mg/kg dose of these medicines administered by gastric perfusion can increase HDL-C/TC ratio of hyperlipidemia mice.

4. Conclusion

The hypolipidemic medicines, also called blood lipid-adjusting medicines, are a series of medicines that can adjust lipid metabolism and can lower overhigh serum TC or TG and/or increase overlow serum HDL-C to improve blood lipid situation. The hypolipidemic medicines, according to their efficacy, can be categorized into 2 groups: the group with a primary effect of TC lowering and a subordinate effect of TG lowering; as well as the group with a primary effect of TG lowering and a subordinate effect of TC lowering. A few medicines that can selectively lower TC or TG The test results show that all of 100, 200, 400, 800 mg/kg dose of these medicines administered by gastric perfusion can lower the serum TC and TG and increase HDL-C/TC ratio in hyperlipidemia mice.

Example 17

Clinical Test

I. Preparation of Tablets
Formulation (1000 Tablets):

| | |
|---|---|
| red peony extract | 240 g |
| *Codonopsis* extract | 60 g |
| Calcium monohydrogen phosphate | 160 g |
| Avicel | 120 g |
| Sodium carboxymethyl starch | 3 g |
| Silicon dioxide | 6 g |
| Magnesium stearate | 6 g |

The tablet based on the above-mentioned formulation was prepared according to the following steps:

Red peony extract, *Codonopsis* extract, calcium monohydrogen phosphate and avicel were mixed and pressed into thin tablets with conditioned dry granulator. The tablets were smashed into granules by granulation machine. The resulting granules were mixed with sodium carboxymethyl starch, magnesium stearate and silicon dioxide, pressed into tablet, coated and packaged.

II. Test Method:

102 persons suffering from simple abnormality of blood lipid were randomly divided into a treated group and a blank control group according to their level of blood lipid, age and gender, and the like. Double-blind randomized, self controlled and cross-over design was employed. The treated group was provided with the tablets produced in part I for a continuous 30-day period, twice a day, 2 tablets for each time. The subjects were kept in regular living and eating ways during the test period.

III. Test Result:

1. Comparison of General Situation Between Treated Group and Control Group

There are 102 subjects participated in the assay. The treated group consists of 22 male and 30 female with average age of 56.63. The control group consists of 19 male and 22 female with average age of 55.18. According to the inquiry of metal situation, sleeping and eating, the subjects were rated into three levels, namely good, moderate and bad, and their blood pressure were measured. As shown in Table 16, generally taking the tablets of the present invention did not have side effects on human body's metal situation, sleeping, eating and blood pressure.

TABLE 16

Comparison of general situation before and after taking the tables

| | Treated group (52) | | | | | | | Control group (50) | | | | | | |
|---|---|---|---|---|---|---|---|---|---|---|---|---|---|---|
| | Before | | | After | | | | Before | | | After | | | |
| | Good | Moderate | Bad | Good | Moderate | Bad | P | Good | Moderate | Bad | Good | Moderate | Bad | P |
| Mental situation | 51 | 1 | 0 | 52 | 0 | 0 | 0.317 | 50 | 0 | 0 | 50 | 0 | 0 | 1.000 |
| Sleeping | 40 | 12 | 0 | 50 | 2 | 0 | 0.002 | 48 | 2 | 0 | 48 | 2 | 0 | 1.000 |
| Eating | 52 | 0 | 0 | 52 | 0 | 0 | 1.000 | 50 | 0 | 0 | 50 | 0 | 0 | 1.000 |
| Excretory situation | 52 | 0 | 0 | 52 | 0 | 0 | 1.000 | 50 | 0 | 0 | 50 | 0 | 0 | 1.000 |
| systolic pressure mmHg | | 137.48 ± 4.46 | | | 135.00 ± 3.84 | | 0.000 | | 137.80 ± 2.51 | | | 135.50 ± 3.39 | | 0.000 |
| Diastolic pressure mmHg | | 82.48 ± 4.73 | | | 81.33 ± 4.02 | | 0.023 | | 81.30 ± 3.62 | | | 81.10 ± 2.91 | | 0.687 |
| Heart rate (times per minute) | | 73.87 ± 11.22 | | | 70.29 ± 6.95 | | 0.000 | | 71.18 ± 9.90 | | | 68.96 ± 6.49 | | 0.003 |

2. Effect of the Test Tablets on Blood, Urine and Feces Routine and Biochemical Indicators The various hematology indicators and hepatorenal function indicators for the treated group and the control group were all within normal ranges, and the urine and feces routine tests did not show significant difference before and after taking up the medicine. It showed that taking up the tablets of this present invention had no side effects on human body's blood, urine and feces routine, and hepatoremal function.

TABLE 17

Measure of blood, urine and feces routine and blood biochemical indicators

| | Before | | | After | | |
|---|---|---|---|---|---|---|
| Indicator | Treated group (52) | Control group (50) | P | Treated group (52) | Control group (50) | P |
| Leukocyte ($10^9$/L) | 6.35 ± 1.02 | 6.21 ± 0.91 | 0.473 | 5.93 ± 0.81 | 5.78 ± 0.70 | 0.313 |
| Erythrocyte ($10^{12}$/L) | 4.38 ± 0.39 | 4.31 ± 0.34 | 0.307 | 4.60 ± 0.44 | 4.54 ± 0.42 | 0.496 |
| Thrombocyte ($10^9$/L) | 197.56 ± 40.68 | 190.22 ± 41.03 | 0.309 | 200.92 ± 53.40 | 191.56 ± 50.12 | 0.364 |
| Hemoglobin (g/L) | 129.56 ± 11.77 | 127.34 ± 10.06 | 0.309 | 136.00 ± 13.20 | 134.26 ± 12.50 | 0.496 |
| Total protein (g/L) | 76.69 ± 3.08 | 77.12 ± 3.37 | 0.503 | 77.71 ± 5.76 | 78.59 ± 4.65 | 0.398 |
| Albumin (g/L) | 45.26 ± 2.39 | 46.17 ± 2.15 | 0.856 | 49.79 ± 3.80 | 49.65 ± 2.84 | 0.829 |
| glutamic-pyruvic transaminase (U/L) | 25.85 ± 12.21 | 28.80 ± 17.83 | 0.33 | 22.63 ± 19.28 | 22.58 ± 13.83 | 0.987 |
| glutamic-oxalacetic transaminase (U/L) | 33.17 ± 13.03 | 33.38 ± 14.92 | 0.941 | 24.93 ± 10.50 | 24.48 ± 8.72 | 0.814 |
| Urea (mmol/L) | 5.94 ± 1.42 | 5.96 ± 1.39 | 0.968 | 4.90 ± 1.49 | 5.10 ± 2.14 | 0.591 |
| Creatinine (mmol/L) | 66.34 ± 14.17 | 68.78 ± 17.36 | 0.438 | 65.72 ± 15.00 | 69.13 ± 15.82 | 0.268 |
| Urine routine | normal | normal | | normal | normal | |
| Feces routine | normal | normal | | normal | normal | |

3. Effect on Total Serum Cholesterol

The treated group showed no significant difference from the control group in terms of the content of total serum cholesterol before taking the tablets, but after administration its content becomed significantly lower than the control group (P<0.01). The content of total serum cholesterol of the treated group after taking the tablets was significantly, 15.7% in average, lower than before (P<0.01). The control group had no significant difference in self comparison. After taking the tables, the difference between the two groups was significantly large (P<0.01) in terms of the content of the total serum cholesterol.

TABLE 18

Effect of taking the tablets on the total serum cholesterol (mmol/L)

| | Observed individual | Before | P | After = | P | Decreasing | P | P[1] |
|---|---|---|---|---|---|---|---|---|
| Treated group | 52 | 5.89 ± 0.84 | 0.966 | 5.00 ± 0.93 | 0.001 | 0.89 ± 1.13 | 0.003 | 0.000 |
| Control group | 50 | 5.90 ± 0.74 | | 5.64 ± 0.88 | | 1.26 ± 0.95 | | 0.058 |

Note:
P[1] is the self comparison between before and after taking the tablets. It was the same in the following table.

4. Effect on Triglyceride

The treated group had no significant difference from the control group in terms of the content of serum triglyceride before taking the tablets, but after administration its content becomed significantly lower than the control group ($P<0.01$). The content of serum triglyceride of the treated group after taking the tablets was significantly, 22.68% in average, lower than before ($P<0.01$). The control group had no significant difference in self comparison. After taking the tables, the difference between the two groups was significantly large ($P<0.01$) in terms of the content of the serum triglyceride.

IV. Conclusion:

In the comparison of the treated group before and after taking the tables, the contents of total serum cholesterol and triglyceride decreased significantly, 15.07% and 22.68% respectively in average. The increase in HDL-C was significant ($P<0.05$), and the content was more than 0.104 mmol/L. The total effective rate of hypolipidemic was 69.2%.

What is claimed is:

1. A hypolipidemic composition consisting of peony extract and *Codonopsis* extract,
    wherein the weight ratio of the peony extract and *Codonopsis* extract in the composition is 0.5-19:1;
    wherein said peony extract is extracted with C1~C8 alcohol-water mixture and said *Codonopsis* extract is extracted with water.

2. The hypolipidemic composition of claim 1, wherein the volume percentage of alcohol in the C1~C8 alcohol-water mixture is between 50% and 95%.

3. The hypolipidemic composition of claim 1, wherein said peony extract is obtained by the following steps:
    grinding dry root of peony plant into peony powders, extracting the powders 1-3 times with, based on the weight of the powder C1~C8 alcohol-water mixture under refluxing, wherein the mixture is 4-10 folds of the weight of the powder;
    combining the extracts, recovering the alcohol, charging the extracts into macroporous adsorbing resin, eluting with 5-70% ethanol;
    collecting and concentrating the eluates, drying to obtain said peony extract;
    said *Codonopsis* extract is obtained by the following steps:
    extracting *Codonopsis* by decocting 1 part raw powder of *Codonopsis* twice with water, based on the weight of the powder, each time for 1.5 hours, wherein the water is 4 parts of the weight of the powder; combining and concentrating the extracts in vacuum.

4. The hypolipidemic composition of claim 1 or 2, wherein the C1~C8 alcohol is ethanol or methanol.

5. The hypolipidemic composition of claim 1 or 2, wherein the composition consisting of peony extract and *Codonopsis* extract, the weight ratio of the peony extract to the Codonopsis extract in the composition is between 1 and 6:1.

6. The hypolipidemic composition of claim 5, wherein the composition consisting of the mixture of peony extract and *Codonopsis* extract, the weight ratio of the peony extract to the *Codonopsis* extract in the composition is between 2 and 3.7:1.

7. The hypolipidemic composition of claim 1, wherein the composition consisting of the mixture of peony extract and *Codonopsis* extract, the weight ratio of the peony extract to the *Codonopsis* extract in the composition is between 1 and 6:1, said peony extract is prepared by the following step:
    Grinding the dry root of peony plant into powders, allowing the powders to pass through 40-mesh screen, and extracting them twice with, based on the weight of the powder 70% ethanol under refluxing, each for 2 hours, wherein the ethanol is 8 folds of the weight of the powder; combining the extracts, recovering the ethanol, and charging the extracts into D101 macroporous adsorbing resin, eluting with 5-70% ethanol; collecting the eluate until no color is observed, then concentrating and drying to obtain said peony extract;
    said *Codonopsis* extract is obtained by the following steps:
    extracting *Codonopsis* by decocting 1 part of *Codonopsis* powder twice with 4 parts of water, based on the weight of the powder, each time for 1.5 hours; combining and concentrating the extracts in vacuum.

8. A method for protecting cells against damage from ox-LDL in a subject, comprising administrating to said subject a composition consisting of peony extract and *Codonopsis* extract, wherein the weight ratio of the peony extract and *Codonopsis* extract in the composition is 0.5-19:1; wherein said peony extract is extracted with C1~C8 alcohol-water mixture, said *Codonopsis* extract is extracted with water.

9. A method for treating high serum total cholesterol in a subject, comprising administrating to said subject a composition consisting of peony extract and *Codonopsis* extract,
    wherein the weight ratio of the peony extract and *Codonopsis* extract in the composition is 0.5-19:1;
    wherein said peony extract is extracted with C1~C8 alcohol-water mixture, said *Codonopsis* extract is extracted with water.

10. A method for treating high serum triglyceride in a subject, comprising administrating to said subject a composition consisting of peony extract and *Codonopsis* extract,
    wherein the weight ratio of the peony extract and *Codonopsis* extract in the composition is 0.5-19:1;
    wherein said peony extract is extracted with C1~C8 alcohol-water mixture, said *Codonopsis* extract is extracted with water.

11. A method for increasing serum high density lipoprotein cholesterol in a subject, comprising administrating to said subject a composition consisting of peony extract and *Codonopsis* extract,
    wherein the weight ratio of the peony extract and *Codonopsis* extract in the composition is 0.5-19:1;

wherein said peony extract is extracted with C1~C8 alcohol-water mixture, said *Codonopsis* extract is extracted with water.

\* \* \* \* \*